(12) United States Patent
Namba et al.

(10) Patent No.: US 9,254,248 B2
(45) Date of Patent: Feb. 9, 2016

(54) INHIBITOR OF ODOR CAUSED BY SOTOLONE

(71) Applicant: Kao Corporaton, Chuo-ku, Tokyo (JP)

(72) Inventors: Aya Namba, Katsushika-ku (JP); Naoko Saito, Utsunomiya (JP); Michiaki Inoue, Cincinnati, OH (US); Tsuyoshi Toyabe, Funabashi (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 14/520,000

(22) Filed: Oct. 21, 2014

(65) Prior Publication Data

US 2015/0110669 A1 Apr. 23, 2015

(30) Foreign Application Priority Data

Oct. 22, 2013 (JP) .................. 2013-219338

(51) Int. Cl.
| | |
|---|---|
| *A61L 9/00* | (2006.01) |
| *A62B 7/08* | (2006.01) |
| *A21D 4/00* | (2006.01) |
| *A61K 8/33* | (2006.01) |
| *A61Q 15/00* | (2006.01) |
| *A61K 8/35* | (2006.01) |
| *A61K 8/49* | (2006.01) |
| *A61Q 19/04* | (2006.01) |

(52) U.S. Cl.
CPC ... *A61K 8/33* (2013.01); *A61K 8/35* (2013.01); *A61K 8/4973* (2013.01); *A61Q 15/00* (2013.01); *A61Q 19/04* (2013.01); *A61K 2800/592* (2013.01); *A61K 2800/5922* (2013.01)

(58) Field of Classification Search
CPC .......... C11D 3/0068; A23L 3/00; A61L 9/01
USPC .............................. 422/5, 123; 426/321, 531
See application file for complete search history.

(56) References Cited

U.S. PATENT DOCUMENTS

| | | | |
|---|---|---|---|
| 2009/0092571 A1* | 4/2009 | Hirano | A61L 9/14 424/76.1 |
| 2013/0303432 A1 | 11/2013 | Hölscher et al. | |
| 2015/0110731 A1 | 4/2015 | Namba et al. | |
| 2015/0111229 A1 | 4/2015 | Namba et al. | |

FOREIGN PATENT DOCUMENTS

| | | |
|---|---|---|
| JP | 2015-080564 A | 4/2015 |
| JP | 2015-081820 A | 4/2015 |

OTHER PUBLICATIONS

Indo, M., Synthetic Flavor and Fragrance, Enlarged and Revised Edition, 2005, The Chemical Daily Co., Ltd., Tokyo, Japan, pp. 348-349.

Karagül-Yüceer, Y et al., "Aroma characterization of fresh and stored-nonfat dry milk," Chapter 8 in Freshness and Shelf Life of Foods, ACS Symposium Series vol. 836, Keith R. Cadwallader et al., eds., Oct. 2002, pp. 108-123, Am. Chem. Soc, Washington, DC.

(Continued)

*Primary Examiner* — Monzer R Chorbaji
(74) *Attorney, Agent, or Firm* — Sterne, Kessler, Goldstein & Fox P.L.L.C.

(57) ABSTRACT

It is intended to provide a substance inhibiting an odor caused by sotolone. The present invention provides an inhibitor of an odor caused by sotolone, comprising an antagonist of an olfactory receptor OR8D1 as an active ingredient.

3 Claims, 3 Drawing Sheets

(56) References Cited

OTHER PUBLICATIONS

Isotani, A, "The fragrance of the old liquor is sweet, and is it hot?", J Biosci Bioengin, 2006, 84(10), p. 417, Society for Bioscience and Bioengineering, Osaka, Japan.

Konig, T et al., "3-Hydroxy-4,5-dimethyl-2(5H)-furanone (Sotolon) causing an off-flavor: elucidation of its formation pathways during storage of citrus soft drinks," J Agric Food Chem, Aug. 1999; 47(8): 3288-3291, Am. Chem. Soc., Washington, DC.

Adipietro, KA et al., "Functional evolution of mammalian odorant receptors," PLoS Genet, 2012, 8(7):e1002821, doi:10.1371/journal.pgen.1002821.

* cited by examiner

Figure 1

Olfactory receptor (400 receptors)

INHIBITOR OF ODOR CAUSED BY SOTOLONE

REFERENCE TO SEQUENCE LISTING SUBMITTED ELECTRONICALLY

The content of the electronically submitted substitute sequence listing, file name 2537_1050000_SequenceListing_ST25.txt, size 4,380 bytes; and date of creation Oct. 10, 2014, filed herewith, is incorporated herein by reference in its entirety.

FIELD OF THE INVENTION

The present invention relates to an inhibitor of an odor caused by sotolone.

BACKGROUND OF THE INVENTION

A large number of malodorous molecules differing in polarity or molecular weight are found in our living environments. Various deodorization methods have been developed so far in order to deodorize these diverse malodorous molecules. In general, such deodorization methods are broadly classified into biological methods, chemical methods, physical methods, and sensory methods. Among the malodorous molecules, highly polar short-chain fatty acids or amines can be deodorized by the chemical method, i.e., neutralization reaction. Sulfur compounds such as thiol can be deodorized by the physical method, i.e., adsorption treatment. Still, there remain a large number of malodorous molecules which cannot be dealt with by the conventional deodorization methods. Also, the deodorization method based on adsorption treatment has a problem that it tends to cause the re-emission of a malodor. In addition, these conventional methods may mask even odors other than the malodor of interest. Thus, a deodorization method which can overcome these problems has been demanded.

Another known method involves deodorizing a malodor by providing another more strongly perceivable order using an aromatic. This method, however, may cause the unpleasant odor of the fragrance. In addition, when masking the malodor by using another odor from, for example, a perfume and an aromatic, an odorous substance which exhibits an effective deodorizing effect on the malodorous substance of interest must be searched. Heretofore, sensory tests by experts have been conducted for the evaluation of odors. Such sensory tests, however, present problems such as the need of fostering experts capable of evaluating odors and low throughputs. Thus, the previous search for an odorous substance which exhibits a deodorizing effect has not been easy to achieve.

In mammals such as humans, the olfactory sense works by the mechanism where odor molecules bind to olfactory receptors on olfactory nerve cells present in the olfactory epithelium lining the nasal cavity to transmit the responses of the receptors thereto to the central nervous system. In humans, approximately 400 olfactory receptors are reportedly found, and genes encoding these receptors account for approximately 3% of all human genes. In general, a set of olfactory receptors is associated with a set of odor molecules. This means that individual olfactory receptors can respond to a plurality of structurally similar odor molecules with different affinities, while individual odor molecules can be recognized by a plurality of olfactory receptors. According to another report, an odor molecule activating a certain olfactory receptor functions as an antagonist inhibiting the activation of a different olfactory receptor. These combined responses of a set of olfactory receptors provide perceivable individual odors.

Accordingly, when a certain odor molecule coexists with a different odor molecule, the different odor molecule may inhibit the response of a receptor corresponding to the certain odor molecule, resulting in the final perception of a different odor. Such a mechanism is called the antagonism of an olfactory receptor. The alteration of an odor caused by this receptor antagonism is a preferred deodorization approach because this approach, unlike the deodorization methods which involve adding an odorant, for example, a perfume and an aromatic, can specifically cancel the perception of a malodor and does not cause an unpleasant odor derived from such an aromatic.

Skin tanning agents (also called self-tanning agents or sunless tanning agents) are skin cosmetics which colors the skin. Mainly, dihydroxyacetone (DHA) is used alone or in combination with, for example, erythrulose as an ingredient which causes the skin color to turn brown. Such an ingredient reacts with the upper layer of the skin to color the skin brown. Although this coloring is believed to proceed through browning reaction, the details of a mechanism underlying this reaction have hardly been elucidated. The browning reaction is also called Maillard reaction in the field of food chemistry. This term refers to the reaction through which a nitrogen-containing compound such as an amino acid or a protein is polymerized with a reduced sugar to form a brown polymer called melanoidin. The Maillard reaction is involved in food coloring or aroma component formation caused by the heating, etc. of foods.

3-Hydroxy-4,5-dimethyl-2(5H)-furanone (sotolone) is a substance known to have an odor expressed as a "curry-like flavor", a "caramel aroma", "burnt sugar", "burn", "spicy", etc. (Non-Patent Documents 1 to 4). Sotolone generally works as an off-flavor having an unpleasant smell similar to that of crude drugs at high concentrations, but produces a syrup-like aroma at low concentrations. Sotolone reportedly induces the response of an olfactory receptor OR8D1 (Non-Patent Document 5).

CITATION LIST

Non-Patent Document

[Non-Patent Document 1] Gosei Koryo—Kagaku To Shohin Chishiki—(Synthetic Flavor and Fragrance—Chemistry and Product Knowledge—in English), 2005, The Chemical Daily Co., Ltd.

[Non-Patent Document 2] ACS Symp Ser., 2002, 836: 108-123

[Non Patent Document 3] Journal of Bioscience and Bioengineering, 2006, 84 (10): 417

[Non-Patent Document 4] J. Agric. Food Chem., 1999, 47 (8): 3288-3291

[Non-Patent Document 5] PLoS Genet, 2012, 8 (7): e1002821

SUMMARY OF THE INVENTION

The present invention provides an inhibitor of an odor caused by sotolone, comprising at least one compound selected from the group consisting of compounds described in Table 1 below as an active ingredient.

TABLE 1

1-(2,3,4,7,8,8a-hexahydro-3,6,8,8-tetramethyl-1H-3a,7-methanoazulen-5-yl)-ethanone;
oxacyclohexadecen-2-one;
citral;
ω-6-hexadecenelactone;
2-benzylideneheptanal;
3-(4-tert-butylphenyl)propanal;
(5E)-3-methylcyclopentadec-5-en-1-one;
1-(5,6,7,8-tetrahydro-3,5,5,6,8,8-hexamethyl-2-naphthalenyl)-ethanone;
7-acetyl-1,2,3,4,5,6,7,8-octahydro-1,1,6,7-tetramethyl-naphthalene; and
muscone

DETAILED DESCRIPTION OF THE INVENTION

The term "masking" in relation to odors as used herein refers to a general approach for canceling or weakening the perception of the odor of interest. The "masking" may include chemical approaches, physical approaches, biological approaches, and sensory approaches. Examples of the masking include: an arbitrary approach for removing an odor molecule causative of the odor of interest from the environment (e.g., adsorption and chemical decomposition of the odor molecule); an approach for preventing the odor of interest from being released to the environment (e.g., containment); and a method which involves adding an odorant, for example, a flavoring agent and a fragrance to reduce the perception of odor of interest.

The term "masking based on olfactory receptor antagonism" as used herein refers to one form of the above-mentioned "masking" in a broad sense. This approach utilizes both of an odor molecule of the odor of interest and a different odor molecule to thereby inhibit a receptor response to the odor molecule of interest by the different odor molecule, resulting in change in odor which is perceived by individuals. The masking based on olfactory receptor antagonism is distinct from the approach of canceling the odor of interest by a different strong odor of, for example, a fragrance, even though these approaches both employ the different odor molecule. One example of the masking based on olfactory receptor antagonism is the case of using a substance, such as an antagonist, which inhibits the response of an olfactory receptor. A substance inhibiting the response of a receptor to an odor molecule responsible for a particular odor can be applied to the receptor to thereby inhibit the response of the receptor to the odor molecule. The odor which is finally perceived by individuals can therefore be changed.

The term "odor caused by sotolone" as used herein can be an odor brought about by sotolone (3-hydroxy-4,5-dimethyl-5(2H)-furanone). The "odor caused by sotolone" as used herein can be typically expressed as, for example, a caramel aroma, a burnt sugar smell, or a curry-like flavor. Also, the "odor caused by sotolone" as used herein can be an unpleasant smell generated by the application of a conventional self-tanning agent to the skin, more specifically, an unpleasant smell expressed as, for example, a "burnt sugar smell" generated by the application of a skin tanning agent containing dihydroxyacetone (DHA) to the skin.

The reported problem of commercially available skin tanning agents (self-tanning agents or sunless tanning agents) is their unique unpleasant smells expressed as earthy, burnt sugar smells, etc. upon application (D. M. Hindenlang and M. E. McDonnell, Cosmetics & Toiletries magazine, 2008, Vol. 123, No. 7, p. 67-74). Thus, improvement in the smells has been demanded. As a result of examining a cause of the unpleasant smell, 3-hydroxy-4,5-dimethyl-2(5H)-furanone (sotolone) produced via methylglyoxal from dihydroxyacetone (DHA) contained in the skin tanning agents has been found to be a causative substance. For reducing such an unpleasant smell attributed to sotolone, it has been required to control the odor of sotolone.

Meanwhile, sotolone can be used as, for example, a flavoring agent for a food or a drink because of its syrup-like aroma, but rather works as an off-flavor when producing too strong an odor. For adjusting the odor of sotolone to proper intensity and achieving the more favorable aroma of a food or a drink, etc., it has been required to control the odor of sotolone.

The present inventor has found that a substance inhibiting the response of the olfactory receptor OR8D1 known to respond to sotolone can inhibit the perception of an odor caused by sotolone by masking based on olfactory receptor antagonism.

Figure 1:
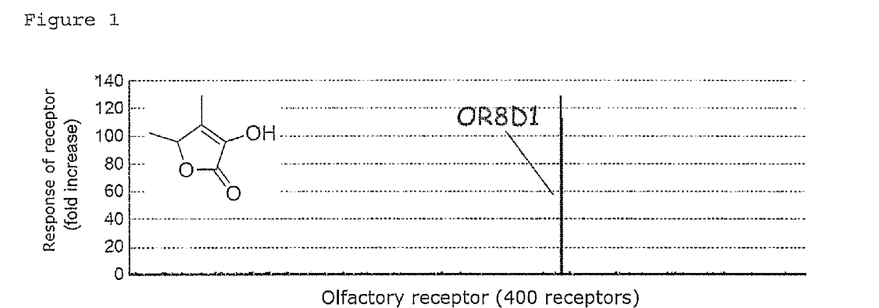
FIG. 1 shows the responses of olfactory receptors to sotolone. The abscissa represents individual olfactory receptors. The ordinate represents response intensity.

As shown in FIG. 1, the present inventor has identified an olfactory receptor OR8D1 as only one receptor responsive to sotolone from among many olfactory receptors. The olfactory receptor OR8D1 refers to an olfactory receptor expressed on a human olfactory cell and is registered as GI: 50897281 in GenBank. OR8D1 is encoded by a gene having the nucleotide sequence represented by SEQ ID NO: 1. This protein consists of the amino acid sequence represented by SEQ ID NO: 2.

Figure 2:
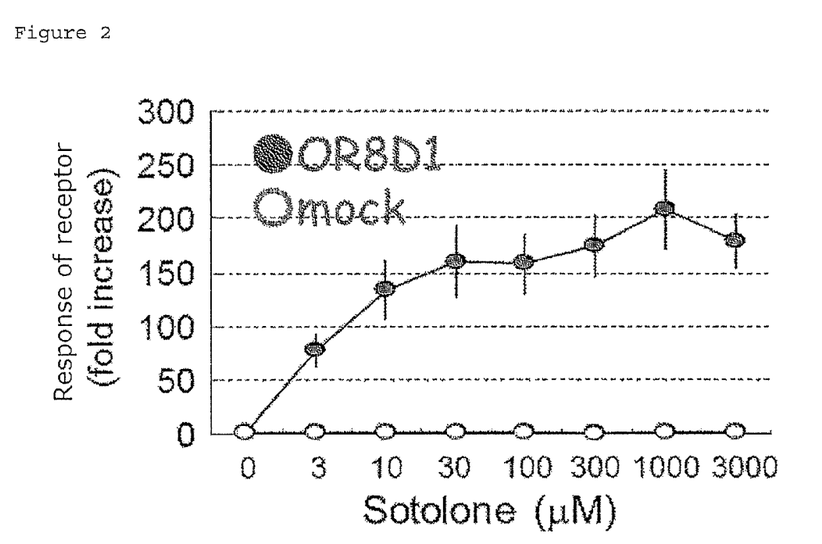
FIG. 2 shows the response of an olfactory receptor OR8D1 to varying concentrations of sotolone. n=3, error bar=±SE.

As shown in FIG. 2, OR8D1 responds to sotolone in a concentration-dependent manner. Thus, a substance inhibiting the response of OR8D1 can change the individual's perception of an odor caused by sotolone in the central nervous system by masking based on olfactory receptor antagonism, resulting in the selective inhibition of the odor caused by sotolone.

The inhibitor of an odor caused by sotolone, provided by the present invention, can selectively deodorize the odor caused by sotolone by masking based on olfactory receptor antagonism. Thus, the inhibitor of an odor caused by sotolone, provided by the present invention can deodorize the odor caused by sotolone, for example, an unpleasant smell generated upon application of conventional self-tanning agents (also called sunless tanning agents), without causing the problems such as the unpleasant odor of a fragrance in conventional deodorization methods using a deodorant or an aromatic.

Thus, according to one aspect, the present invention provides an inhibitor of an odor caused by sotolone, comprising a substance inhibiting the response of an olfactory receptor OR8D1 as an active ingredient. The inhibitor of an odor caused by sotolone according to the present invention functions as an antagonist of OR8D1. In other words, the inhibitor of an odor caused by sotolone according to the present invention comprises an antagonist of OR8D1 as an active ingredient. Thus, the inhibitor of an odor caused by sotolone according to the present invention can change the individual's perception of an odor caused by sotolone in the central nervous system by masking based on olfactory receptor antagonism, resulting in the inhibition of the odor caused by sotolone.

Examples of the active ingredient in the inhibitor of an odor caused by sotolone according to the present invention include the following compounds:

1-(2,3,4,7,8,8a-hexahydro-3,6,8,8-tetramethyl-1H-3a,7-methanoazulen-5-yl)-ethanone(acetylcedrene);
oxacyclohexadecen-2-one (Habanolide(R));
citral;
ω-6-hexadecenelactone(ambrettolide);
2-benzylideneheptanal(amylcinnamic aldehyde);
3-(4-tert-butylphenyl)propanal(bourgeonal);
(5E)-3-methylcyclopentadec-5-en-1-one (Muscenone(R) Delta);
1-(5,6,7,8-tetrahydro-3,5,5,6,8,8-hexamethyl-2-naphthalenyl)-ethanone (Tonalid(R));
7-acetyl-1,2,3,4,5,6,7,8-octahydro-1,1,6,7-tetramethyl-naphthalene (Iso E Super); and
muscone.

These compounds are OR8D1 antagonists. Each of these OR8D1 antagonists can inhibit the response of the olfactory receptor OR8D1 to sotolone by 40% or more, preferably 50% or more, more preferably 75% or more, compared with that in the absence of the antagonist. In other words, the response of the olfactory receptor OR8D1 to sotolone in the presence of the antagonist is reduced to 60% or less, preferably 50% or less, more preferably 25% or less, of the response of the receptor in the absence of the antagonist.

Among these OR8D1 antagonists, preferred examples of the active ingredient in the inhibitor of an odor caused by sotolone include 1-(2,3,4,7,8,8a-hexahydro-3,6,8,8-tetramethyl-1H-3a,7-methanoazulen-5-yl)-ethanone(acetylcedrene).

The inhibitor of an odor caused by sotolone according to the present invention comprises at least one compound selected from the group consisting of the OR8D1 antagonists listed above as an active ingredient. For example, the active ingredient in the inhibitor of an odor caused by sotolone according to the present invention may be at least one compound, for example, any one compound alone or any two or more compounds in combination, selected from the group consisting of the OR8D1 antagonists listed above. Preferably, the inhibitor of an odor caused by sotolone according to the present invention is composed essentially of at least one compound selected from the group consisting of the OR8D1 antagonists.

As shown in Table 3, each of these OR8D1 antagonists inhibits the response of the olfactory receptor OR8D1 to sotolone. These compounds have previously been known as flavor materials, but have not been known to have the function of antagonizing the response of the olfactory receptor to sotolone to selectively inhibit the odor caused by sotolone.

A commercially available product can be purchased as any of the OR8D1 antagonists listed above (see Motoichi Indo, "Gosei Koryo—Kagaku To Shohin Chishiki—(Synthetic Flavors—Chemistry and Product Knowledge—in English)", enlarged and revised edition, The Chemical Daily Co., Ltd., issued in March 2005). These antagonists are available from, for example, Firmenich S. A., Givaudan S. A., International Flavors & Fragrances Inc., Takasago International Corp., and Kao Corp.

According to another aspect of the present invention, the OR8D1 antagonists listed above can each be used as an active ingredient for inhibiting an odor caused by sotolone, for example, a caramel aroma, a burnt sugar smell, or a curry-like flavor, or an unpleasant smell (e.g., a burnt sugar smell) generated by the application of a self-tanning agent to the skin or upon application of a product containing dihydroxyacetone (DHA).

In one embodiment, the OR8D1 antagonists listed above can each be contained as an active ingredient for inhibiting an odor caused by sotolone in a compound or a composition for inhibiting an odor caused by sotolone. Alternatively, the OR8D1 antagonists listed above can be used for production of an inhibitor of an odor caused by sotolone or for production of a compound or a composition for inhibiting an odor caused by sotolone.

In one embodiment, the OR8D1 antagonists listed above can each be used as an active ingredient for inhibiting an odor caused by sotolone in every compound or composition desired to inhibit an odor caused by sotolone or in every environment desired to inhibit an odor caused by sotolone. Alternatively, the OR8D1 antagonists can each be used as an active ingredient for inhibiting an odor caused by sotolone, for production of a compound or a composition desired to inhibit an odor caused by sotolone. Examples of the compound or the composition desired to inhibit an odor caused by sotolone include skin tanning agents (also called self-tanning agents or sunless tanning agents), for example, a skin tanning agent containing dihydroxyacetone (DHA) as a coloring agent and other skin tanning agents which employ browning reaction, and other products containing DHA. Sotolone, which is an aroma component contained in a food or a drink, may rather work as an off-flavor at high levels. Thus, other examples of the compound or the composition desired to inhibit an odor caused by sotolone include foods or drinks desired to reduce the off-flavor of sotolone having a high concentration, and compositions containing the foods or the drinks.

The inhibitor of an odor caused by sotolone, and the compound or the composition for inhibiting an odor caused by sotolone may appropriately contain an additional ingredient having a deodorizing effect according to the purpose, in addition to any of the OR8D1 antagonists listed above. Any of generally known deodorants having a chemical or physical deodorizing effect can be used as the additional ingredient having a deodorizing effect. Examples thereof include malodor reducing active ingredients extracted from plants (e.g., green tea extracts), organic acids, various amino acids and their salts, glyoxal, oxidants, flavonoids, catechins, polyphenols, porous substances (e.g., active carbon and zeolite), inclusion complexes such as, for example, cyclodextrins, photocatalysts, and various masking agents. The inhibitor, and the compound or the composition for inhibiting an odor caused by sotolone may further comprise an optional ingredient which is generally added to a deodorant or a smell-preventing agent.

According to a further aspect, the present invention provides a method of inhibiting an odor caused by sotolone, comprising the step of coexistence between any of the OR8D1 antagonists listed above and the odor caused by sotolone.

In one embodiment, this method involves applying at least one compound selected from the group consisting of the OR8D1 antagonists listed above to an individual, accordingly the antagonist coexists with the odor caused by sotolone, wherein the individual is in need of inhibition of the perception of the odor caused by sotolone in the presence of the odor, preferably in need of inhibition of the perception of the odor caused by sotolone by masking based on olfactory receptor antagonism. As a result, the antagonist binds to OR8D1 to inhibit the response of OR8D1 to sotolone. Masking based on olfactory receptor antagonism therefore takes place to thereby inhibit the odor caused by sotolone. In the method, preferred examples of the OR8D1 antagonist are the same as those mentioned above in relation to the inhibitor of an odor caused by sotolone.

In the method of the present invention, the individual can be any mammal without particular limitations and is preferably a human. More specifically, examples of the individual in need of inhibition of the perception of the odor caused by sotolone in the method of the present invention include humans who use skin tanning agents (also called self-tanning agents or sunless tanning agents), more specifically, a skin tanning agent containing dihydroxyacetone (DHA) as a coloring agent or other skin tanning agents which employ browning reaction, humans who use other products containing DHA, and humans who desire reduction in the odor caused by sotolone from foods or drinks.

In one embodiment of the method of the present invention, the OR8D1 antagonist is added to a compound or a composition containing sotolone. This reduces the response of the olfactory receptor to sotolone contained in the compound or the composition and inhibits the individual's perception of the odor caused by sotolone, resulting in the inhibition of the odor caused by sotolone. In another embodiment, the OR8D1 antagonist is added to a compound or a composition which may produce sotolone. This reduces the response of the olfactory receptor to sotolone produced from the compound or the composition and inhibits the individual's perception of the odor caused by sotolone, resulting in the inhibition of the odor caused by sotolone. Examples of the compound or the composition which may produce sotolone include skin tanning agents, for example, a skin tanning agent containing dihydroxyacetone (DHA) as a coloring agent and other skin tanning agents which employ browning reaction, and other products containing DHA.

The following composition, production method, use, or method will be further disclosed herein as an exemplary embodiment of the present invention. However, the present invention is not intended to be limited by these embodiments.

<1> An inhibitor of an odor caused by sotolone, comprising at least one compound selected from the group consisting of the compounds described in Table 1 as an active ingredient.

<2> Use of at least one compound selected from the group consisting of the compounds described in Table 1 for inhibition of an odor caused by sotolone.

<3> Use of at least one compound selected from the group consisting of the compounds described in Table 1 for production of an inhibitor of an odor caused by sotolone.

<4> At least one compound selected from the group consisting of the compounds described in Table 1 for use in the inhibition of an odor caused by sotolone.

<5> A method of inhibiting an odor caused by sotolone, comprising coexistence between at least one compound selected from the group consisting of the compounds described in Table 1 and the odor caused by sotolone.

<6> The inhibitor, the use, the compound, or the method according to any of <1> to <5>, wherein the at least one compound selected from the group consisting of the compounds described in Table 1 is preferably 1-(2,3,4,7,8,8a-hexahydro-3,6,8,8-tetramethyl-1H-3a,7-methanoazulen-5-yl)-ethanone.

EXAMPLES

Hereinafter, the present invention will be described more specifically with reference to Examples.

Example 1

Identification of Olfactory Receptor Responding to Sotolone

1) Cloning of Human Olfactory Receptor Gene

On the basis of sequence information registered in GenBank, each human olfactory receptor gene was cloned by PCR with Human Genomic DNA Female (G1521: Promega Corp.) as a template. Each gene thus amplified by PCR was inserted into a pENTR vector (Invitrogen Corp.) according to the manual. A NotI-AscI site present on the pENTR vector r was recombined into a NotI-AscI site prepared downstream of Flag-Rho tag sequence on a pME18S vector.

2) Preparation of pME18S-Human RTP1S Vector

A gene (GenBank GI: 50234917) encoding a human receptor transport protein, RTP1S was inserted into the EcoRI-XhoI site of the pME18S vector.

3) Preparation of Olfactory Receptor-Expressing Cell

HEK293 cells expressing each of 400 types of human olfactory receptors were prepared. Each reaction solution having the composition shown in Table 2 was prepared, then left standing for 15 minutes in a clean bench, and then added to each well of a 96-well plate (Becton, Dickinson and Company). Subsequently, the HEK293 cells ($3 \times 10^5$ cells/cm$^2$) were inoculated thereto at 100 µL/well and then cultured at 37° C. for 24 hours in an incubator kept at 5% $CO_2$.

TABLE 2

| | |
|---|---|
| OPTI-MEM (GIBCO) | 50 µL |
| Human olfactory receptor gene (inserted into N-terminally Flag-Rho-tagged pME18S vector) | 0.075 µg |
| pGL4.29 (fluc2P-CRE-hygro, Promega) | 0.03 µg |
| pGL4.75 (hRluc-CMV, Promega) | 0.03 µg |
| pME18S-human RTP1S vector | 0.03 µg |
| lipofectamine 2000 (Invitrogen) | 0.4 µL |

4) Luciferase Assay

The olfactory receptors expressed on the HEK293 cells are conjugated with intracellular Gαs to activate adenylate cyclase, thereby increasing intracellular cAMP levels. In this study, their responses to sotolone were measured using luciferase reporter gene assay which involved monitoring increase in intracellular cAMP level as luminescence intensity derived from a firefly luciferase gene (fluc2P-CRE-hygro). In addition, the cells were cotransfected with the reporter gene and a fusion gene (hRluc-CMV) of a *Renilla* luciferase ene downstream of a CMV promoter for use as an internal standard for correcting transfection efficiency or an error in the number of cells.

A medium was removed from the cultures prepared in the preceding paragraph 3). To the resulting cultures, 75 µL of a solution containing sotolone (1 mM) prepared with a CD293 medium (Invitrogen Corp.) was added. The cells were cultured for 2.5 hours in a $CO_2$ incubator to express the luciferase genes at sufficient levels in the cells. The luciferase activity was measured using Dual-Glo™ luciferase assay system (Promega Corp.) according to the instruction manual of the product. Firefly luciferase-derived luminescence intensity induced by stimulation with sotolone was divided by luminescence intensity in the cells without sotolone stimulation to calculate a value as fold increase, which was in turn used as an index for response intensity.

5) Results

As a result of measuring the responses of 400 types of olfactory receptors to sotolone (1 mM) in this Example, the olfactory receptor OR8D1 already reported to respond to sotolone (Non-Patent Document 1) exhibited a response to sotolone. By contrast, the other olfactory receptors did not respond to sotolone (FIG. 1).

Example 2

Concentration-Dependent Response of OR8D1 to Sotolone

The olfactory receptor OR8D1 (GenBank GI: 50897281, SEQ ID NO: 2) was expressed, together with human RTP1S, on HEK293 cells by the same procedures as in Example 1 and then examined for the concentration dependence of its response to varying concentrations of sotolone (0, 3, 10, 30, 100, 300, 1000, and 3000 μM). As a result, OR8D1 exhibited a concentration-dependent response to sotolone (FIG. 2).

Example 3

Identification of OR8D1 Antagonist 228 types of test substances were examined for their antagonistic activity against the response of the olfactory receptor OR8D1 to sotolone.

Sotolone (100 μM) and each test substance (100 μM) were added to HEK293 cells allowed to express the olfactory receptor OR8D1 by the same procedures as in Example 2. The response of the olfactory receptor was measured to evaluate change in receptor response caused by the addition of the test substance.

The rate of inhibition of the receptor response by the test substance was calculated as follows: firefly luciferase-derived luminescence intensity (Y) in the olfactory receptor OR8D1-expressing cells without sotolone stimulation was subtracted from firefly luciferase-derived luminescence intensity (X) induced by stimulation with sotolone alone to determine receptor activity (X−Y) based on the stimulation with sotolone alone. Likewise, the luminescence intensity (Y) in the cells without sotolone stimulation was subtracted from luminescence intensity (Z) induced by stimulation with the mixture of sotolone and the test substance to determine receptor activity (Z−Y) in the presence of the test substance. The rate of reduction in the receptor activity (Z−Y) in the presence of the test substance with respect to the receptor activity (X−Y) based on the stimulation with sotolone alone was calculated according to an expression shown below to determine the rate of inhibition of the receptor response by the test substance. In this assay, a plurality of independent duplicate experiments was performed. An average of the experiments in each run was obtained.

$$\text{Rate of inhibition (\%)} = \{1-(Z-Y)/(X-Y)\}\times 100$$

As a result, 10 types of test substances had 40% or higher rate of inhibition of the response of OR8D1 to sotolone (reduced the response to 60% or less), demonstrating that these test substances have antagonistic activity against OR8D1 (Table 3).

TABLE 3

| | |
|---|---|
| 75% or more rate of inhibition (response was reduced to 25% or less; very strong antagonist) | 1-(2,3,4,7,8,8a-hexahydro-3,6,8,8-tetramethyl-1H-3a,7-methanoazulen-5-yl)-ethanone (acetylcedrene) |
| 50% or more rate of inhibition (response was reduced to 50% or less; strong antagonist) | Oxacyclohexadecen-2-one (Habanolide(R)) Citral ω-6-Hexadecenelactone (ambrettolide) 2-Benzylideneheptanal (amylcinnamic aldehyde) 3-(4-tert-Butylphenyl)propanal (bourgeonal) (5E)-3-Methylcyclopentadec-5-en-1-one (Muscenone(R) Delta) 1-(5,6,7,8-tetrahydro-3,5,5,6,8,8-hexamethyl-2-naphthalenyl)-ethanone (Tonalid(R)) 7-Acetyl-1,2,3,4,5,6,7,8-octahydro-1,1,6,7-tetramethyl-naphthalene (Iso E Super) |
| 40% or more rate of inhibition (response was reduced to 60% or less; weak antagonist) | Muscone |

Example 4

Evaluation on Ability of OR8D1 Antagonist to Inhibit Odor of Sotolone

Each test substance having antagonistic activity against OR8D1, identified in Example 3, was confirmed by a sensory test for its ability to inhibit the odor of sotolone.

Each panelist smelled 0.5 g of sotolone (1%)-containing cloth supplemented with 0.5 μL of a flavoring agent, and then evaluated the intensity of the odor of sotolone compared with cloth non-supplemented with the flavoring agent. The sensory evaluation test was conducted by 3 panelists. The odor of sotolone was evaluated as 1 when strongly perceivable and as 5 when not perceivable.

Figure 3:
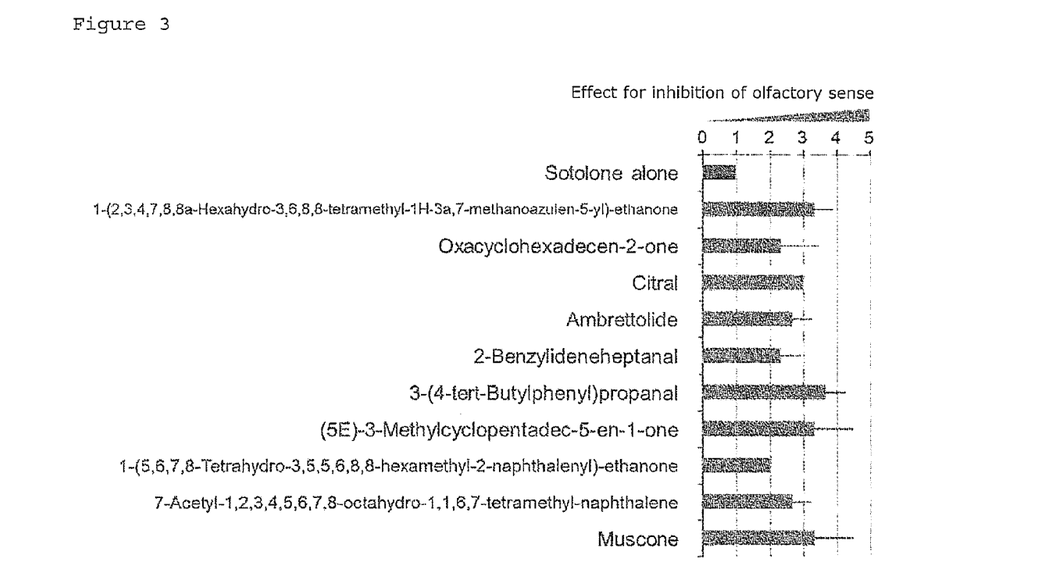
FIG. 3 shows results of sensory evaluation on the inhibitory effects of various compounds on the odor of sotolone. n=3, error bar=±SE.

As a result, all the 10 types of test substances demonstrated to inhibit the response of OR8D1 to sotolone in Example 3 inhibited the odor of sotolone (FIG. 3).

The invention claimed is:

1. A method of inhibiting an odor caused by sotolone, comprising coexistence between at least one compound selected from the group consisting of the following compounds:
- oxacyclohexadecen-2-one;
- 1-(2,3,4,7,8,8a-hexahydro-3,6,8,8-tetramethyl-1H-3a,7-methanoazulen-5-yl)-ethanone;
- 2-benzylideneheptanal;
- 3-(4-tert-butylphenyl)propanal;
- (5E)-3-methylcyclopentadec-5-en-1-one;
- 1-(5,6,7,8-tetrahydro-3,5,5,6,8,8-hexamethyl-2-naphthalenyl)-ethanone and
- 7-acetyl-1,2,3,4,5,6,7,8-octahydro-1,1,6,7-tetramethyl-naphthalene, and an odor caused by sotolone.

2. The method according to claim 1, wherein the coexistence is application of the at least one compound to an individual in need of inhibition of the perception of the odor caused by sotolone in the existence of an odor caused by sotolone.

3. The method according to claim 1, wherein the coexistence is mixing the at least one compound with sotolone or with a composition comprising sotolone.

* * * * *

SEQUENCE LISTING

```
<160> NUMBER OF SEQ ID NOS: 2

<210> SEQ ID NO 1
<211> LENGTH: 927
<212> TYPE: DNA
<213> ORGANISM: Homo sapiens
<220> FEATURE:
<223> OTHER INFORMATION: DNA encoding human OR8D1

<400> SEQUENCE: 1
atgaccatgg aaaattattc tatggcagct cagtttgtct tagatggttt aacacagcaa      60
```

```
gcagagctcc agctgccect cttcctcctg ttcctgggaa tctatgtggt cacagtagtg    120
ggcaacctgg gcatgattct cctgattgca gtcagccctc tacttcacac ccccatgtac    180
tatttcctca gcagcttgtc cttcgtcgat ttctgctatt cctctgtcat tactcccaaa    240
atgctggtga acttcctagg aaagaagaat acaatccttt actctgagtg catggtccag    300 ctcttttttct tgtggtctt tgtggtggct gagggttacc tcctgactgc catggcatat    360
gatcgctatg ttgccatctg tagcccactg ctttataatg cgatcatgtc tcatgggtc    420 tgctcactgc tagtgctggc tgccttcttc ttgggctttc tctctgcctt gactcataca    480
agtgccatga tgaaactgtc cttttgcaaa tcccacatta tcaaccatta cttctgtgat    540
gttcttcccc tcctcaatct ctcctgctcc aacacacacc tcaatgagct tctactttt    600 atcattgcgg ggtttaacac cttggtgccc accctagctg ttgctgtctc ctatgccttc    660
atcctctaca gcatccttca catccgctcc tcagagggcc ggtccaaagc ttttggaaca    720
tgcagctctc atctcatggc tgtggtgatc ttctttgggt ccattacctt catgtatttc    780
aagccccctt caagtaactc cctggaccag agaaggtgt cctctgtgtt ctacaccacg    840
gtgatcccca tgctgaaccc tttaatatac agtctgagga ataaggatgt gaagaaagca    900
ttaaggaagg tcttagtagg aaaatga                                        927
```

<210> SEQ ID NO 2
<211> LENGTH: 308
<212> TYPE: PRT
<213> ORGANISM: Homo sapiens
<220> FEATURE:
<223> OTHER INFORMATION: Polypeptide of human OR8D1

<400> SEQUENCE: 2

```
Met Thr Met Glu Asn Tyr Ser Met Ala Ala Gln Phe Val Leu Asp Gly
1               5                   10                  15

Leu Thr Gln Gln Ala Glu Leu Gln Leu Pro Leu Phe Leu Leu Phe Leu
            20                  25                  30

Gly Ile Tyr Val Val Thr Val Val Gly Asn Leu Gly Met Ile Leu Leu
        35                  40                  45

Ile Ala Val Ser Pro Leu Leu His Thr Pro Met Tyr Tyr Phe Leu Ser
    50                  55                  60

Ser Leu Ser Phe Val Asp Phe Cys Tyr Ser Ser Val Ile Thr Pro Lys
65                  70                  75                  80

Met Leu Val Asn Phe Leu Gly Lys Lys Asn Thr Ile Leu Tyr Ser Glu
                85                  90                  95

Cys Met Val Gln Leu Phe Phe Val Val Phe Val Val Ala Glu Gly
            100                 105                 110

Tyr Leu Leu Thr Ala Met Ala Tyr Asp Arg Tyr Val Ala Ile Cys Ser
        115                 120                 125

Pro Leu Leu Tyr Asn Ala Ile Met Ser Ser Trp Val Cys Ser Leu Leu
    130                 135                 140

Val Leu Ala Ala Phe Phe Leu Gly Phe Leu Ser Ala Leu Thr His Thr
145                 150                 155                 160

Ser Ala Met Met Lys Leu Ser Phe Cys Lys Ser His Ile Ile Asn His
                165                 170                 175

Tyr Phe Cys Asp Val Leu Pro Leu Leu Asn Leu Ser Cys Ser Asn Thr
            180                 185                 190

His Leu Asn Glu Leu Leu Leu Phe Ile Ile Ala Gly Phe Asn Thr Leu
        195                 200                 205
```

```
Val Pro Thr Leu Ala Val Ala Val Ser Tyr Ala Phe Ile Leu Tyr Ser
    210                 215                 220

Ile Leu His Ile Arg Ser Ser Glu Gly Arg Ser Lys Ala Phe Gly Thr
225                 230                 235                 240

Cys Ser Ser His Leu Met Ala Val Val Ile Phe Phe Gly Ser Ile Thr
                245                 250                 255

Phe Met Tyr Phe Lys Pro Pro Ser Ser Asn Ser Leu Asp Gln Glu Lys
                260                 265                 270

Val Ser Ser Val Phe Tyr Thr Thr Val Ile Pro Met Leu Asn Pro Leu
        275                 280                 285

Ile Tyr Ser Leu Arg Asn Lys Asp Val Lys Lys Ala Leu Arg Lys Val
    290                 295                 300

Leu Val Gly Lys
305
```